United States Patent
Buisman et al.

(10) Patent No.: US 8,805,577 B2
(45) Date of Patent: Aug. 12, 2014

(54) METHOD AND APPARATUS FOR DISPENSING MEDICATION

(75) Inventors: Harm Jacob Buisman, Eindhoven (NL); Georgio Mosis, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 230 days.

(21) Appl. No.: 13/145,881

(22) PCT Filed: Jan. 18, 2010

(86) PCT No.: PCT/IB2010/050219
§ 371 (c)(1),
(2), (4) Date: Jul. 22, 2011

(87) PCT Pub. No.: WO2010/084450
PCT Pub. Date: Jul. 29, 2010

(65) Prior Publication Data
US 2011/0282489 A1      Nov. 17, 2011

(30) Foreign Application Priority Data
Jan. 23, 2009   (EP) .................................... 09151179

(51) Int. Cl.
*G06F 17/00*   (2006.01)

(52) U.S. Cl.
USPC ............ 700/237; 700/236; 700/241; 700/244

(58) Field of Classification Search
USPC ................. 700/237, 236, 240, 241, 244, 242
See application file for complete search history.

(56) References Cited

U.S. PATENT DOCUMENTS

| 4,725,997 | A  | * | 2/1988  | Urquhart et al. ................. 368/10 |
| 4,785,969 | A  | * | 11/1988 | McLaughlin ................. 700/237 |
| 5,267,174 | A  | * | 11/1993 | Kaufman et al. ............. 700/242 |
| 5,408,443 | A  | * | 4/1995  | Weinberger ....................... 221/3 |
| 5,805,051 | A  | * | 9/1998  | Herrmann et al. ......... 340/309.4 |
| 6,102,855 | A  | * | 8/2000  | Kehr et al. ..................... 221/289 |
| 7,269,476 | B2 | * | 9/2007  | Ratnakar ....................... 700/236 |
| 7,715,277 | B2 | * | 5/2010  | de la Huerga ..................... 705/2 |
| 2005/0033223 | A1 |  | 2/2005 | Herrera |
| 2006/0259187 | A1 | * | 11/2006 | Berg ............................. 700/231 |
| 2008/0059228 | A1 | * | 3/2008 | Bossi et al. ....................... 705/2 |
| 2008/0203107 | A1 |  | 8/2008 | Conley et al. |

FOREIGN PATENT DOCUMENTS

| GB | 2205306 A     | 12/1988 |
| JP | 5502529 A     | 4/1993  |
| JP | 2007334805 A  | 12/2007 |

* cited by examiner

*Primary Examiner* — Timothy Waggoner

(57) ABSTRACT

A method for dispensing at least two medications to a patient, the method comprising the steps of: automatically dispensing at least one first medication to a patient according to a predetermined dosage level; receiving (203) a request from the patient for a second medication; determining (207, 215) the total dispensed dosage of the at least one first medication and the second medication for the patient; providing (209, 211, 213, 217, 219, 223) an indication if the determined dispensed dosage is equal to or greater than a predetermined maximum dosage; and dispensing (225) the requested second medication if the determined dispensed dosage is less than or equal to the predetermined maximum dosage.

15 Claims, 2 Drawing Sheets

METHOD AND APPARATUS FOR DISPENSING MEDICATION

FIELD OF THE INVENTION

The present invention relates to method and apparatus for dispensing medication. In particular, but not exclusively, it relates to dispensing at least one medication on demand.

BACKGROUND OF THE INVENTION

Use of devices for automatically dispensing medication is becoming increasingly popular. These devices enable the patient and unskilled caregivers to administer complex medication regimes providing patients with greater independence. One known type of dispenser is the MD.2 pill dispenser (http://www.epill.com/md2.html). This device allows family members to serve as caregivers by programming the dispenser, refilling its contents and having data about medication taken transmitted to the caregiver's computer. The patient's medication management can also be constantly monitored in real time using an Internet connection, for example. Alternatively, the device can be set up to issue a phone call to up to five designated family members or caregivers if the patient fails to take their pills within, say, 90 minutes of the assigned time.

The MD.2 pill dispenser dispenses medication in re-usable sealable cups. Each cup is preloaded with a required dosage of medication to be taken at any one time. The cups are then dispensed at predetermined time intervals. The dispenser holds 60 medication cups, dispensing up to 6 cups per day. It has the capacity to store 3-4 weeks of medications for most patients.

If refills are needed, alerts and/or phone calls can be made to the caregiver. The dispenser includes a user interface to provide the patient with alerts to remind them to take their medication and provide a reminder of any instructions such as "take with food". It can also provide an early dose feature in which a patient can take their medication early within the constraints of their dosage regimes. Such a system is disclosed by U.S. Pat. No. 4,725,997. Although U.S. Pat. No. 4,725,997 allow changes to the existing dosage regimes, it does not provide complementing existing medication to be taken with a "take-as-needed" medication.

SUMMARY OF THE INVENTION

The present invention seeks to provide a complete medication management system for at least two medications.

This is achieved according to a first aspect of the present invention by a method for dispensing at least two medications to a patient, the method comprising the steps of: automatically dispensing at least one first medication to a patient according to a predetermined dosage level; receiving a request from the patient for a second medication; determining the total dispensed dosage of the at least one first medication and the second medication for the patient; providing an indication if the determined dispensed dosage is equal to or greater than a predetermined maximum dosage; and dispensing the requested second medication if the determined dispensed dosage is less than or equal to the predetermined maximum dosage.

This is also achieved according to a second aspect of the present invention by apparatus for dispensing at least two medications to a patient, the apparatus comprising: a first dispensing channel for automatically dispensing at least one first medication according to a predetermined dosage level; a second dispensing channel for dispensing a second medication upon receipt of a request from the patient; a processor for determining the total dispensed dosage of the at least one first medication and the second medication for the patient; means for providing an indication if the determined dispensed dosage is equal to or greater than a predetermined maximum dosage.

In this way, medication is dispensed according to an existing dosage regime and can be complemented, in single management system, with a second medication, such as "take-as-needed" medication. This enables a maximum dosage to be monitored, avoiding over dosage and adverse interactions between the first and second medications. Controlling the maximum dosage level also controls the timing so that the first and second medications can be taken at suitable time intervals.

The first and second medications may be dispensed via separate dispensing channels such that the first and second medications can be dispensed independently as required. However, the maximum dosage takes into account the amount of medication dispensed by the separate channels such that the timing of dispensing of the first and second medication not only depends on the dispensing from its specific channel, but also on the dispensing of the other medications from the other channels, i.e. there is a cross-dependency between the channels.

In an embodiment of the present invention, an indication may also be provided if at least one predetermined requirement for dispensing the dosage of the at least one first and/or the second medication is not met, for example, a timer may be used to monitor the time interval between dispensing the first and second medications to prevent adverse interactions between the medications. The indication may be to provide instructions of particular condition to be met on taking the next dosage, such as "take with food" or to indicate that the medication should be dispensed at a particular time of day.

The indication may be provided in a way that the dosage of the second medication is dispensed and may be accompanied by a visual and/or audio alert to the patient. In this way the patient can decide whether or not to take the dispensed dosage on the basis of the form of the alert. The dispensing of the second medication may be recorded and transmitted to a caregiver and/or health professional as an alert or as a record on their computer. The health professional can then remotely assess the progress of the patient on the basis of their usage of the second medication. For example, the second medication may provide pain relieve and the health professional can assess the level of discomfort of the patient and reassess their medication or care if necessary.

Alternatively the indication may be to prevent dispensing of the dosage of the second medication and issuing a visual and/or audio alert to the patient. Therefore dangerous dosage levels can be avoided or level of the second medication can be controlled so as to not have an adverse effect on the treatment provided by the first medication. The patient can be made aware of this by an alert.

The visual and/or audio alert may be transmitted to a remote node such as the computer/telephone of a caregiver or health professional. Alternatively, or in addition to transmission of the alert, data of usage of the medications made by the patient may be transmitted to such a remote node. For example, data may be transmitted concerning the dosage of the first and second medications dispensed, the requests made for the second medication, which requests were dispensed and which were not, whether any medications was due to be dispensed but were not dispensed and hence not taken by the patient. The caregiver and health professional is therefore made aware of the levels of use made by the patient. Further the alert may be transmitted to indicate that a dosage has been missed. This provides the caregiver or health professional of a complete record of the patient medication use over a period. This can be particularly effective in allowing assessment of the patient's condition and enable the caregiver or health professional to deal with any adverse effects from taking the combination of medications. This provides an improved overview and assessment of the patient's care and needs.

In requesting the second medication, the patient may be alerted to the current dosage levels and make a confirmation that they wish the second medication to be dispensed.

The dispenser may be portable or, alternatively, it may comprise a remote indicator that can issue a reminder to a patient to take medication, even when out-of-range of the dispenser. The dispenser may collect and store data about when medication is removed from the dispenser or when a reminder is missed. The dispenser may also collect additional data in the form of a questionnaire which can be use to reinforce correct behavior (e.g. take dissolved in water) or detect side-effects (i.e. headaches) which might indicate an intervention. This data may be communicated for further analysis to a remote server, which may analyze the data to generate interventions from a health professional, call centre or caregiver. The stored data may be read by a local device for the direct benefit of the patient or caregiver.

BRIEF DESCRIPTION OF DRAWINGS

For a more complete understanding of the present invention, reference is made to the following description in conjunction with the accompanying drawings, in which.

DETAILED DESCRIPTION OF AN EMBODIMENT OF THE INVENTION

Figure 1:
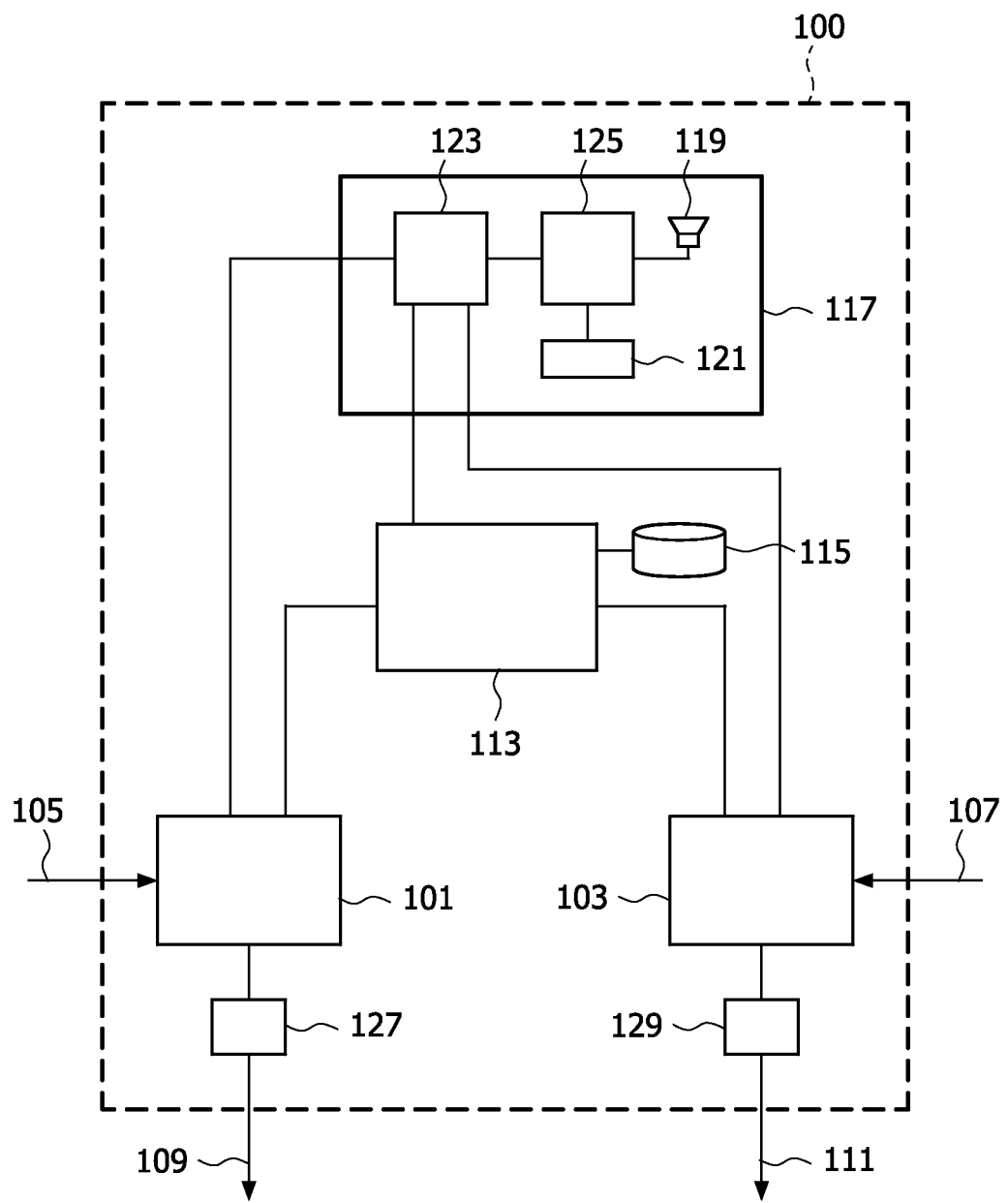
FIG. 1 illustrates a simplified schematic of apparatus according to an embodiment of the present invention.

With reference to FIG. 1, the apparatus 100 comprises first and second dispensing channels 101, 103. The first and second dispensing channels 101, 103 are connected to a first and second loading mechanism 105, 107 respectively. The first and second dispensing channels 101, 103 comprise first and second output ports 109, 111. Although, two output ports are shown here in this embodiment, the first and second dispensing channels 101, 103 may share a single output port. Sensing which medication has been dispensed may be combined with a sensor within the output port and activation of either the first or second dispensing channels 101, 103 or, alternatively, having separate sensors positioned at the exit of the first and second dispensing channels 101, 103 or, alternatively, by mere activation of a dispensing channel with no additional sensors. The first and second output ports 109, 111 comprise first and second sensors 127, 129 respectively. The apparatus 100 further comprises a processor 113 comprising an internal storage means (not shown here) or, alternatively, connected to an external storage means 115 as shown. The processor 113 also comprises a first and second timers or counters (not shown here). The processor 113 is connected to the first and second dispensing channels 101, 103 and indication means 117. The indication means 117 is also connected to the first and second dispensing channel 101, 103. The indication means 117 includes control means 123 for controlling dispensing of first and second medication from the first and second dispensing channels 101, 103, a transmitter 125, a user interface 121, including a display and at least one push button. The user interface 121 may also include a keypad or the like to allow programming of the apparatus 100 via the processor 113. The indication means 117 may also include a loud speaker 119 and/or buzzer (not shown) and at least one LED (not shown). Although 2 dispensing channels are shown here, it is understood that any number of dispensing channels may be provided as required.

Operation of the apparatus of FIG. 1 will now be described in more detail with reference to FIG. 2. The operation of the apparatus 100 will be described with reference to a specific example in which a patient takes a first medication every 5 hours (a predetermined dosage) and a second medication to be requested to be taken as needed but not to be taken within 2 hours of the first medication.

The apparatus 100 is loaded with individual dosages of a first medication within the first dispensing channel 101 and a second medication within a second dispensing channel 103 via the loading mechanisms 105, 107 respectively. The medication may be loaded into the dispensing channels in the form of an individual dosage in a sealable plastic cup which is loaded into a mechanism that dispenses the cup when required or requested. This can be particularly useful for dispensing a complex mix of pills or medication in liquid form. The first and/or second medications may be in the form of a pill which is preloaded into a blister pack. The blister packs is made available and connected wirelessly to the first and second dispensing channels 101, 103. With respect to the specific example above, the first medication is loaded into the first dispensing channel 101 and the second medication is loaded into the second dispensing channel 103.

The first timer (or counter) of the processor 113 is reset upon loading of the first medication and the second timer is reset upon loading of the second medication. This can be manually reset to give the time the first and/or second medication was last dispensed or set automatically on the basis of the time the first and/or second medication was dispensed. In the case of the specific example above, the first timer is reset on the basis of when the first medication was last dispensed by the first dispensing channel 101 and the second timer is reset upon dispensing of the first medication. At 5 hour intervals maintained by the timer of the processor 113, the first medication is dispensed via the first output port 109 of the first dispensing channel 101. The first medication may be dispensed by first providing the patient with an alert or reminder via the loudspeaker, buzzer, LED and/or display. It may provide instructions of how the medication is taken. The patient can then push a button on the user interface to cause the first medication to be dispensed out of the first dispensing channel 101 via the first output port 109. The first sensor 127 of the first output port 109 senses the dispensing of the first medication and records the time the medication was dispensed. Alternatively, the first output port 109 has no sensor and merely registers that the first medication has been dispensed upon confirmation made by the patient in pushing a button of the user interface. However, use of the first sensor 127 ensures that a medication is dispensed and registered, avoiding an error in the event that the first dispensing channel 101 is empty. This is transferred to the processor for storing in the storage means 115 and the indication means 117 for transmitting via the transmitter 125 to a remote node such as a computer/server of a caregiver or health professional. Upon sensing the dispensing of the first medication, the first timer of the processor 113 is reset, to start counting the next 5 hour interval.

Figure 2:
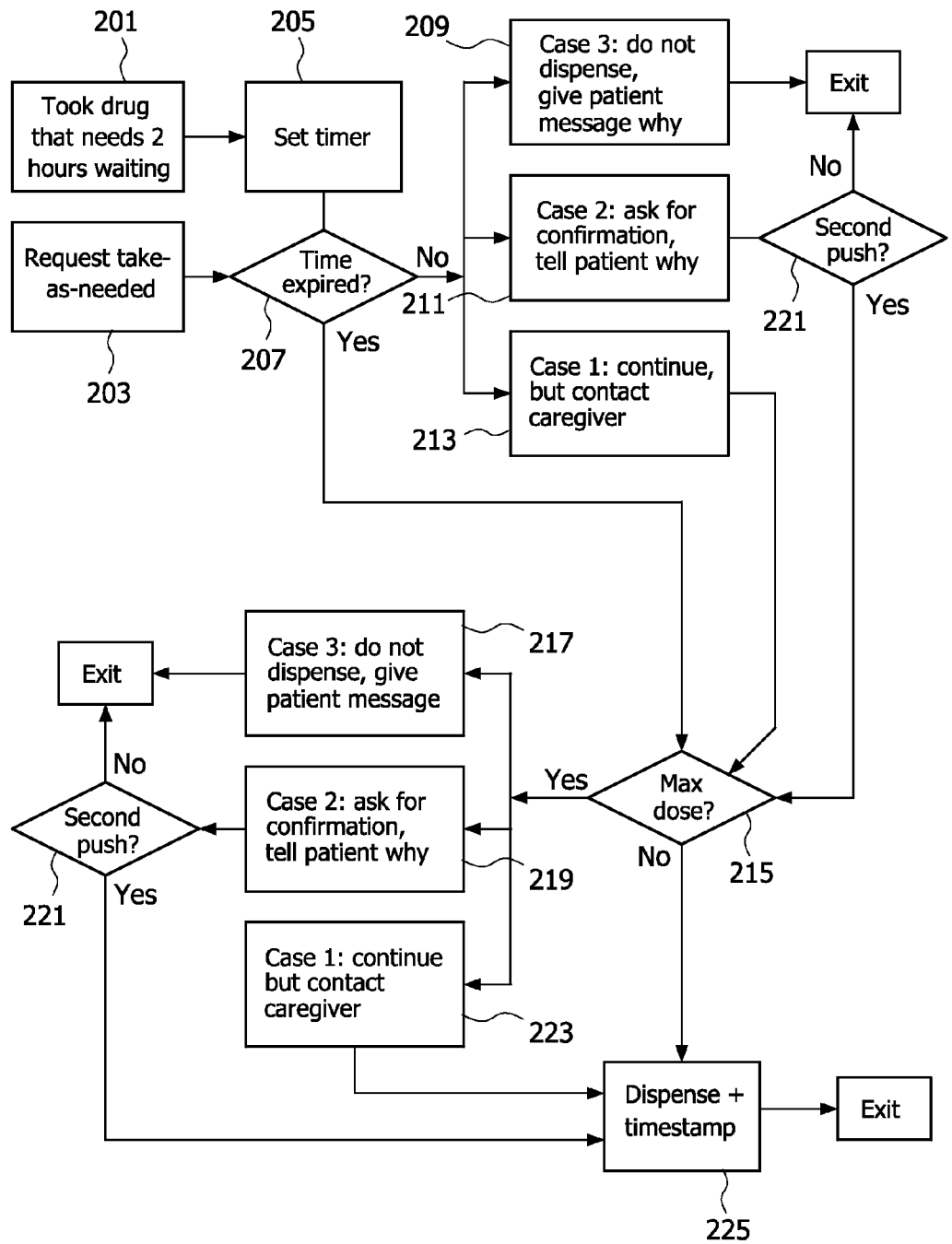
FIG. 2 illustrates a flowchart of a method according to an embodiment of the present invention.

As shown in FIG. 2, the patient may also request a second medication to be "taken-as-needed". This may be a different medication to the first medication or may be similar to the first medication. A second timer is set, step 205 to record 2 hour intervals from when the first medication was last dispensed, step 201 from the first dispensing channel as sensed by the first sensor 127 of the first output port 109. A request for the second medication is received by the patient via the user interface, step 203. The timing of the request is compared to the time the first medication was last dispensed, step 207. If the 2 hour interval has not been reached, the indication means 117 provides an indication to this effect. The indication means 117 will either prevent dispensing of the second medication, step 209, via the control means 123 and provide the patient with an indication to this effect via a message displayed on the display of the user interface 121, for example, lighting a LED or activating the buzzer or output an audio alert such as a voice message via the loud speaker 119. The time that the second medication was requested but not dispensed is recorded in the storage means 115. Or, alternatively, the indication means 117 may ask the patient for confirmation, step 211, via the display of the user interface 121 or loudspeaker 119 and awaits confirmation, step 213. The indication means 117 will give a voice warning or visual warning that it is not safe to take the new dose, the patient has to push the button of the user interface 121 again (send confirmation) to ignore the warning. If no confirmation is received, the apparatus can then record the time when the patient requested the second medication and chose not to dispense it. Or, alternatively, the indication means 117 continues and contacts a caregiver or health professional via the transmitter to the caregiver/health professional's computer or telephone or the like, step 213, to warn the caregiver or health professional that the patient exceeded his dosage.

If the time has expired (more than 2 hours have passed) or following step 213 or upon receipt of a confirmation, the dosage level of the dispensing first and second medication is compared to a maximum dosage level, step 215. If the maximum dosage level is exceeded, the indication means 117 will either prevent dispensing of the second medication, step 217, via the control means 123 and provide the patient with a indication to this effect via a message displayed on the display of the user interface 121, for example, lighting a LED or activating the loud speaker 119 and/or buzzer. Or, alternatively, the indication means 117 may ask the patient for confirmation, step 219 and awaits confirmation, step 221. Or, alternatively, the indication means 117 continues and contacts a caregiver or health professional via the transmitter to the caregiver/health professional's computer or telephone or the like, step 223, to warn the caregiver or health professional that the patient exceeded his maximum dosage (the device may also be set to send a message the moment the maximum dosage is reached).

If the maximum dosage level has not been exceeded, or following step 223, or upon receipt of a confirmation, the second medication is dispensed via the second dispensing channel 103, step 225. The sensor of the second output port 111 detects that the second medication has been dispensed and records the time the medication was dispensed. This is transferred to the processor for storing in the storage means 115 and the transmitter 125 of the indication means 117 for transmitting to a remote node such as a computer/server of a caregiver or health professional.

In the alternative embodiment in which the first and second medications are in the form of pills stored in a blister pack. The blister packs include the first and second sensors for detecting when a blister is opened and a pill dispensed. This is communicated to the processor 113 via first and second dispensing channels and the control of the medication is as described above. The blister packs may also include the indication means 117 to provide an indication to the patient etc.

In cases when medication should be taken in a prescribed way after removal from the package, for example, crushed and dissolved in water, or taken before/after meals, the user may be reminded to confirm compliant behavior by activating a sensor to record a yes/no answer to questions pre-printed on the indication means 117.

In cases when patients subjective experience of their state of health should be captured, for example when side-effects are suspected or to otherwise help in diagnosis, the user may be reminded to confirm compliant behavior by activating a sensor to record a yes/no answer to questions provided by the indication means 117.

The data of the storage means 115 can be uploaded to a remote server and/or local processing device such as a PC. The data can be analyzed to detect compliancy patterns and, depending on the answers to questions, obtain indications regarding the outcome, side-effects, etc. This data can also be combined with other time-stamped data from monitors, for example a blood pressure monitor, to provide the caregiver with a rich source of information on which to base follow-ups and interventions.

The apparatus 100 may also be used to record events. For example, in pregnancy it is important to record accurately the moment at which the first contraction occurs, when the waters break, and when the contractions achieve a certain frequency. This may not be related to a medication event but the accurate data is useful to a professional. In these cases, only the answers to questions will be logged and may be reported.

The predetermined dosage levels of the medication can be programmed into the apparatus in a variety of formats, for example, the dosage may comprise a cut-off for a single dose, a cut-off for total amount of drug allowed in a 24-hour period, and a cut-off for an entire course of therapy.

Although embodiments of the present invention have been illustrated in the accompanying drawings and described in the foregoing detailed description, it will be understood that the invention is not limited to the embodiments disclosed, but is capable of numerous modifications without departing from the scope of the invention as set out in the following claims.

The invention claimed is:

1. A method for dispensing at least two medications to a patient, the method comprising with a processor the steps of:
   controlling a first dispensed channel to dispense a predetermined first medication dosage of a first medication to a patient;
   receiving a request from said patient for a second medication dosage of a second medication which second medication interacts with the first medication;
   determining a total dosage of said dispensed first medication and said requested second medication for said patient;
   providing an indication if said determined total dispensed dosage is equal to or greater than a predetermined maximum total dosage; and
   dispensing said requested second medication if said determined dispensed dosage is less than or equal to said predetermined maximum total dosage.

2. The method according to claim 1, wherein the method further comprises the step of:
   with an alarm or display, providing an indication if at least one predetermined requirement for dispensing at least one of said first medication dosage of said one first medication and the second medication dosage of the second medication is not met.

3. The method according to claim 1, wherein said step of providing the indication if said determined dosage is equal to or greater than the predetermined maximum total dosage comprises the steps of:
dispensing said requested second medication dosage of said second medication; and
issuing an alert to said patient indicating the maximum predetermined total dosage has been reached and the requested second medication is still being dispensed.

4. The method according to claim 1, wherein said step of providing the indication if said determined total dosage is equal to or greater than the predetermined maximum total dosage comprises the steps of:
preventing the dispensing of said requested second medicine dosage of said requested second medication; and
issuing an alert to said patient indicating the maximum predetermined total dosage has been reached and the medication is not being dispensed.

5. The method according to claim 3, wherein said step of issuing the alert to said patient comprises the step of:
with a transmitter, transmitting said alert and information data relating to the first and second medication dispensed, the second medication requests, and first and second medications not taken by the patient to a remote node.

6. The method according to claim 1, wherein the step of providing the indication if said determined dosage is equal to or greater than the predetermined maximum total dosage comprises the steps of:
requesting a confirmation from said patient;
dispensing said requested second medication in response to receiving said confirmation; and
preventing the dispensing of said requested second medication in response to no confirmation being received.

7. An apparatus for dispensing at least two interacting medications to a patient, the apparatus comprising:
a first dispensing channel which dispenses at least one first medication of a predetermined first dosage;
a second dispensing channel which dispenses a second medication in response to receipt of a request from said patient to dispense a second dosage of the requested second medication;
a processor configured to determine a total dosage of said at least one first medication and said requested second medication; and
an indicator which provides an alert to said patient in response to said determined total dosage being equal to or greater than the predetermined maximum total dosage.

8. The apparatus according to claim 7, wherein the processor is further configured to:
control said second dispensing channel to prevent the second dispensing channel from dispensing said second medication in response to the determined total dosage of the dispensed at least one first medication and the requested second medication exceeding the predetermined maximum total dosage.

9. The apparatus according to claim 7, wherein the indicator includes a display which provides a visual alarm to said patient in response to the determined total dosage being equal to or greater than the predetermined maximum total dosage.

10. The apparatus according to claim 7, wherein the indicator includes a loud speaker which provides an audio alarm to said patient in response to the determined total dosage being equal to or greater than the predetermined maximum total dosage.

11. The apparatus according to claim 7, further including:
a transmitter which transmits the alert and information data relating to medication dispensed, medication requests and medications not taken to a remote node.

12. An apparatus for dispensing at least two medications which adversely interact to a patient, the apparatus comprising a processor programmed to:
control a first dispensing channel to dispense a prescribed medication on a predetermined schedule;
control a second dispensing channel to dispense a take-when-needed medication on request;
receive a request from the patient for a dose of the take-when-needed medication;
determine whether there is an adverse interaction between a previously delivered dosage of the prescribed medication and the requested dose of the take-when-needed medication and send an indication to the patient if the adverse interaction determined; and
determine if the previously dispensed dosage of the prescribed medication and the requested dose of the take-when-needed medication for the patient is equal to or greater than a predetermined maximum total dosage.

13. The apparatus according to claim 12, wherein the processor is further programmed to:
in response to determining the adverse interaction, warn the patient of the adverse interaction and dispense the requested dose of the take-when-needed medication.

14. The apparatus according to claim 12, wherein the processor is further programmed to:
in response to determining the adverse interaction, warn the patient of the adverse interaction and prevent the take-when-needed medication from being dispensed.

15. The apparatus according to claim 12, wherein the processor is further programmed to, in response to determining the adverse interaction:
request a confirmation from said patient;
control the second dispensing channel to dispense the requested dose of the take-when-needed medication in response to receiving said confirmation; and
prevent the second dispensing channel from dispensing of the requested dose of the take-when-needed medication in response to no confirmation being received.

\* \* \* \* \*